United States Patent [19]

Fare et al.

[11] Patent Number: 5,111,221
[45] Date of Patent: May 5, 1992

[54] RECEPTOR-BASED SENSOR

[75] Inventors: Thomas L. Fare, Washington, D.C.; Frances S. Ligler, Potomac, Md.

[73] Assignee: United States of America as represented by the Secretary of the Navy, Washington, D.C.

[21] Appl. No.: 544,442

[22] Filed: Jun. 27, 1990

Related U.S. Application Data

[62] Division of Ser. No. 193,625, May 13, 1988, abandoned.

[51] Int. Cl.⁵ .................. H01L 29/66; H01L 29/96
[52] U.S. Cl. .................. 357/25; 357/23.1; 437/228; 435/291; 204/416; 204/418
[58] Field of Search .................. 357/25, 23.1, 30 D, 357/30 P, 23.15; 324/71.1, 71.5; 435/291, 176, 180; 204/403, 416, 418; 436/501, 525, 805; 437/228

[56] References Cited

U.S. PATENT DOCUMENTS

| | | | |
|---|---|---|---|
| 4,104,090 | 8/1978 | Pogge | 148/175 |
| 4,144,636 | 3/1979 | Burkhardt et al. | 29/590 |
| 4,490,216 | 12/1984 | McConnell | 204/1 T |
| 4,562,157 | 12/1985 | Lowe et al. | 435/291 |
| 4,645,583 | 2/1987 | Shiri et al. | 204/435 |
| 4,728,882 | 3/1988 | Stanbro et al. | 324/61 R |
| 4,874,499 | 10/1989 | Smith et al. | 204/403 |
| 4,874,500 | 10/1989 | Madou et al. | 204/412 |
| 4,881,109 | 11/1989 | Ogawa | 357/25 |
| 4,885,077 | 12/1989 | Karakelle et al. | 204/403 |
| 4,909,921 | 3/1990 | Ito | 204/403 |

OTHER PUBLICATIONS

"Medical Instrumentation", Ligler et al., Feb. 25, 1988.
NRL Labstracts, 1988 NRL Newsletter, May 27, 1988.

*Primary Examiner*—Rolf Hille
*Assistant Examiner*—David Ostrowski
*Attorney, Agent, or Firm*—Thomas E. McDonnell; Barry A. Edelberg

[57] ABSTRACT

This invention relates to a semiconductor substrate having a porous surface and to the amperometric receptor-based sensors formed with the substrate. More specifically, this invention pertains to the substrate in the form of a bipolar junction transistor having a porous hydrophilic surface directly on its base wherein the surface forms a support for an amperometric sensor. The invention also pertains to the methods of making and using the substrate and sensor.

27 Claims, 3 Drawing Sheets

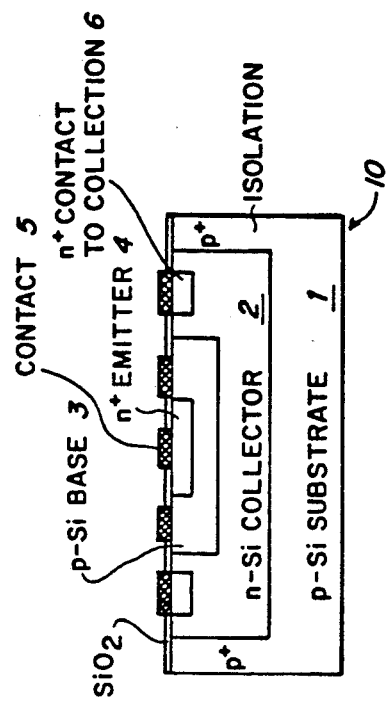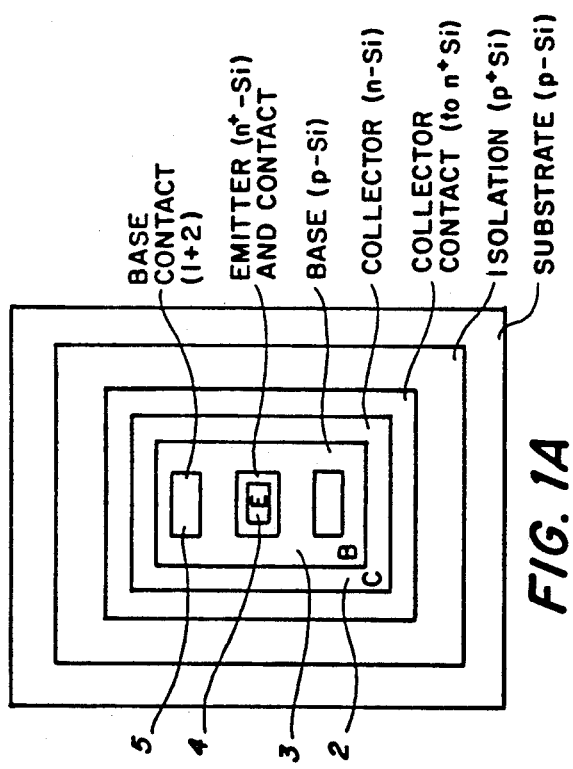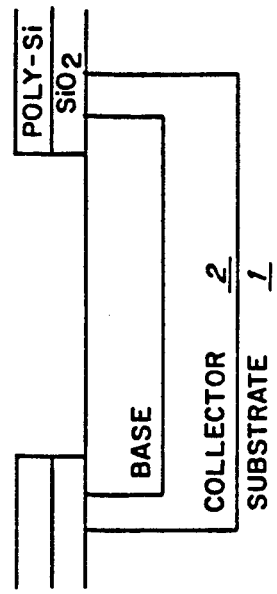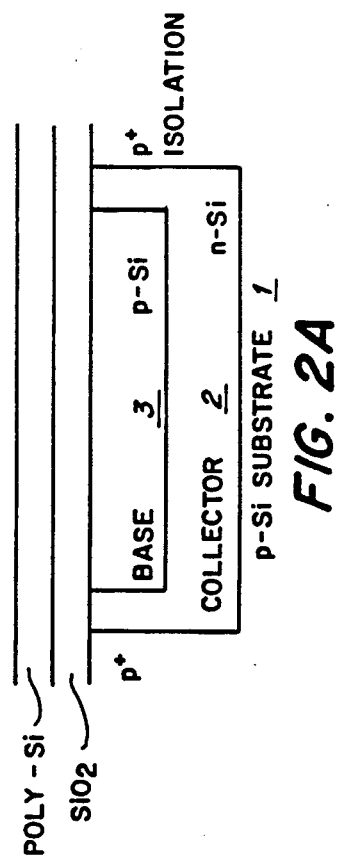
FIG. 1A
FIG. 1B
FIG. 2A
FIG. 2B

OUTPUT = $V_1 - V_2$

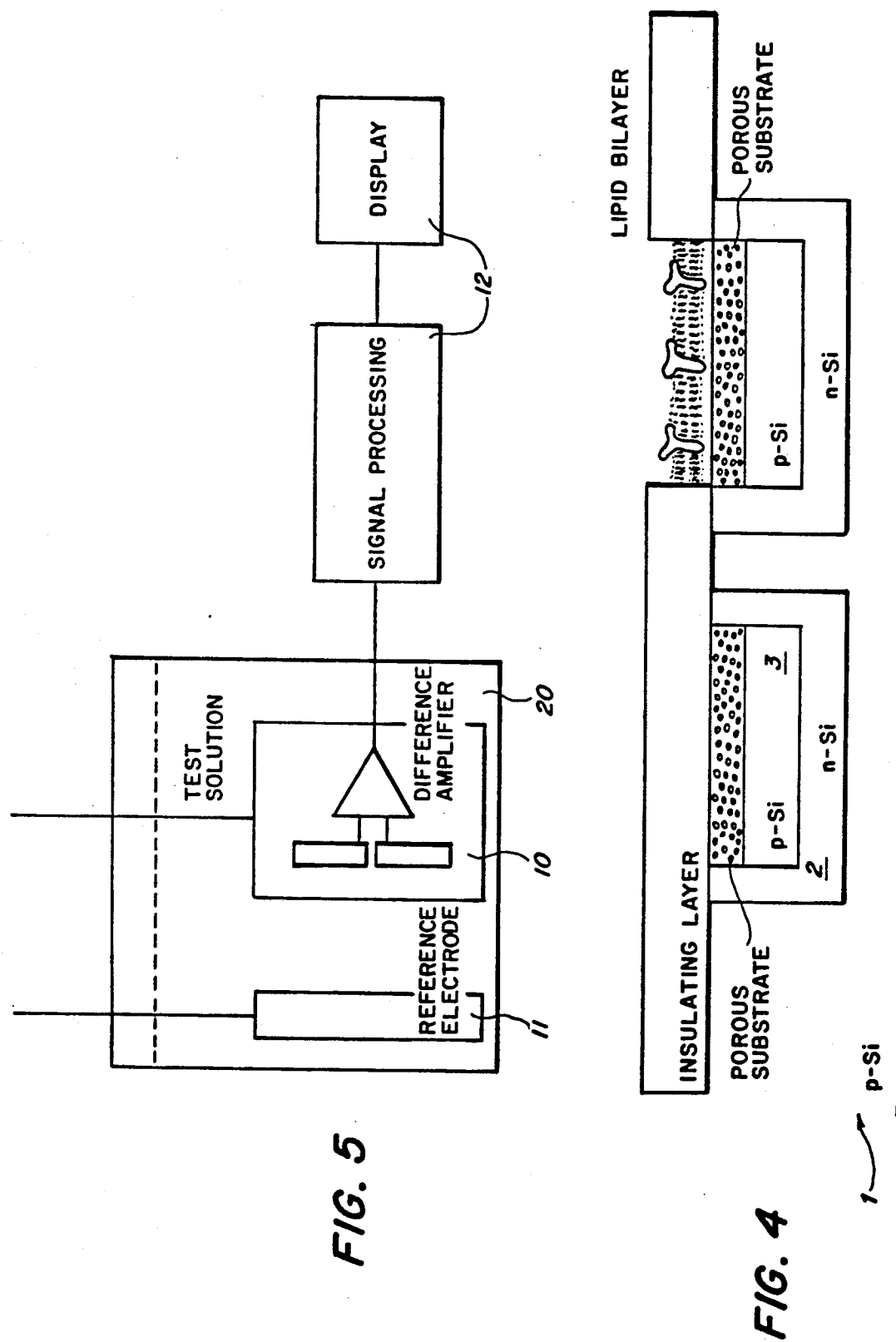

RECEPTOR-BASED SENSOR

This is a division of co-pending application Ser. No. 07/193,625 filed on May 13, 1988 now abandoned.

BACKGROUND OF THE INVENTION

1. Field of the Invention

This invention relates to semiconductor materials and methods of preparation and, more particularly, to amperometric receptor-based sensors.

2. Description of the Prior Art

Sensor devices which use receptor molecules for chemical detection are based primarily on two schemes: amperometric and capacitive. An amperometric scheme most closely mimics the physiological functions of the receptor molecules.

In the prior art such as Jarvis, *Biosensors: Today's Technology, Tomorrow's Products* pp.155, SEAI Technical Publications, Madison, Ga., 1986, or Turner et al., *Biosensors: Fundamentals and Applications*, p. 770, Oxford University Press, New York, N.Y., 1987, a lipid bilayer is deposited onto a porous, hydrophilic film, which, in turn, is deposited onto a support electrode. Ligand-activated ion channels or voltage-gated ion channels are co-deposited with the lipid membrane, or inserted after the lipid membrane has been deposited. The support electrode and a reference electrode are placed in an electrolyte bath of fixed pH or a known ionic strength When a channel is excited by a stimulus in this bath, an ion current flows through the excited channel from the reference electrode to the support electrode. This is also discussed in Yager, United States SIR No. H201, issued Jan. 6, 1987.

In these type of prior art devices it is essential that the lipid membrane serves as a highly impermeable seal against the free flow of the ions from one electrode to the other (the background current, part of the noise in the measurement), or else the ion current through the receptor is drowned out in the background current. A good seal can be measured as a high (electrical) impedance for current flow.

As taught by Arya et al. "Langmuir-Blodgett Deposition of Lipid Films on Hydrogel as a Basis for Biosensor Development," *Anal. Chim. Acta* 173: 331-336, 1985, and Thompson et al., "The Structure and Electrochemical Properties of a Polymer Supported Lipid Biosensor," *Anal. Chim. Acta* 117: 133-155, 1980, the usual configuration of the amperometric electrode consists of a silver-silver chloride wire or thin film upon which a thin layer of a hydrophilic, porouspolymer (such as polyhydroxyethylmethacrylate, PHEMA) has been deposited. A lipid bilayer is deposited either by a Langmuir-Blodgett dipping technique, or by brushing on a mixture of lipids and solvent onto the polymer, and allowing the bilayer to thin on the electrode (similar to the technique developed for black lipid membranes, BLM's).

These techniques suffer from several deficiencies: first, there is some difficulty getting the polymer to adhere to the silver-silver chloride; second, there is a problem with getting the lipids to adhere to the polymer to give a high impedance seal, which, in turn, contributes to the noise of the measurement; third, it is inherently difficult to remove some of the background noise because of the large area of these electrodes.

Efforts have been made to reduce the area of these devices, but these efforts have been limited by the art's ability to control the deposition of the polymer. The primary drawback caused by this problem is an inability to control the background current contribution to the circuit noise.

The second approach, the capacitive technique, has been developed for use with a non-porous substrate upon which two electrodes in the form of interdigitated metallic fingers have been deposited. This approach is described in articles by M. Eldefrawi et al.,"Acetylcholine Receptor-Based Biosensor", Third Annual Conference on Receptor-Based Biosensors, Laurel, Md. Sep. 11-12, 1987, and A. L. Newman et al., "Advances in Capacitive Affinity Sensor Technology", Third Annual Conference on Receptor-Based Biosensors, Laurel, Md., Sep. 11-12, 1987.

The lipid-protein films are deposited on top of the metallic fingers. The substrate is placed in a reference bath, and the A.C. impedance of the films is measured either between the fingers of the two deposited electrodes, or between a reference electrode and one of the finger electrodes. The main drawback to this technique is that it suffers from a lack of sensitivity. The measurement does not offer any inherent advantage for amplifying the signal without introducing a similar amplification of the background noise.

The problem with both of these techniques is that if one wishes to increase the signal from the receptors, either one increases the surface area of the device or one increases the number of receptors per unit area. If the concentration of the receptor molecules is limited, then one would like to fabricate a device which will give the largest signal per receptor concentration.

One way to increase the signal is to make the devices larger; however, an increase in the surface area of these devices also results in an increase in the noise contribution, which may not be filtered out of the signal. In addition, it is desirable to make these devices as small as possible to avoid defects in the thin lipid bilayer. One would ultimately like to increase the receptor signal without increasing the noise (also called increasing the signal-to-noise ratio, SNR) and to do this for the smallest area possible.

In U.S. Pat. No. 4,562,157, Lowe et al. describes a sensor in which two or more biochemical species are positioned on the surface of an FET transistor. The biochemical material is essentially printed on the surface of the FET by lithographic means. The device works by measuring capacitance.

Burkhardt et al., in U.S. Pat. Nos. 4,144,636 and 4,057,832, describes a sensor which utilizes a porous silicon layer protected by an oxide layer on a silicon dioxide base. The device can only measure humidity.

These prior art devices are not shown as sensitive sensors capable of detecting a broad range of reactive entities while maintaining a low signal to noise ratio.

SUMMARY OF THE INVENTION

Accordingly, it is an object of this invention to detect any moiety or entity that will create a current on contact with the sensor surface.

Also, it is an object of this invention to increase the signal to noise ratio of the receptor signal over the background noise of the sensor circuit.

Further, it is an object of this invention to increase the amplification of the signal in a sensor circuit.

An additional object of this invention is to efficiently connect biosensors to electronic circuits.

Another object of this invention is to provide a transistor particularly adapted to operating as part of a sensor.

In addition, it is an object of this invention to provide a high impedance seal over the transistor used in the sensor.

Also, it is an object of this invention to detect the presence of more than one active moiety at a time.

Yet another object of this invention is to simplify the design and manufacture of highly sensitive and discriminating sensors.

These and other objects can be achieved by a sensor having a semiconductor substrate and a porous surface wherein the porous surface is protected by a receptor film adhered over at least the porous surface. The combination forms an amperometric receptor-based sensor.

More specifically, this invention pertains to the substrate in the form of an electronic device such as a bipolar junction transistor having a porous hydrophilic surface directly on its base wherein the surface is protected by a thin oxide layer and the oxide layer forms a support for the receptor film. The film is selected to detect specific moieties or reactive entities or combinations of them.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein:

FIG. 1A is a side view of a transistor embodiment of this invention.

FIG. 1B is a plan view of a transistor embodiment of this invention.

FIG. 2A is a side view of a step in the preparation of this invention.

FIG. 2B is a view of a subsequent step in the preparation of this invention to that shown in FIG. 2A.

FIG. 4 is a view of subsequent steps in the preparation of this invention to that shown in FIGS. 2A and 2B.

FIG. 5 is a diagram of an embodiment of this invention in use.

DESCRIPTION OF THE PREFERRED EMBODIMENT

Figure 6:
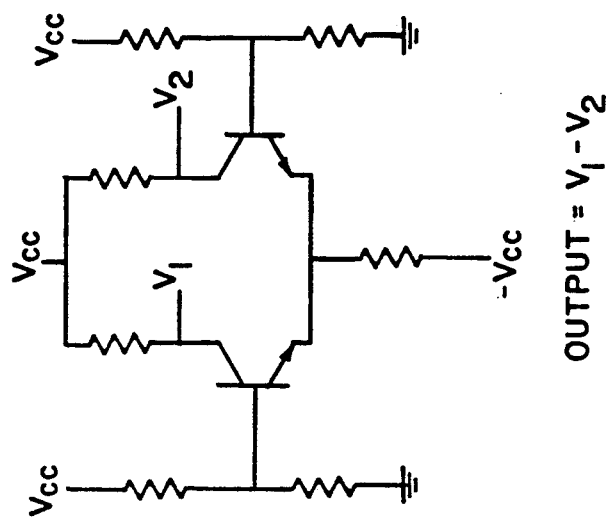
FIG. 6 is a wiring diagram illustrating an alternative application of the sensor of this invention.

This invention is directed to a sensor which integrates a semiconductor substrate material with a highly selective receptor film. The semiconductor substrate contains a porous portion or area either in or upon its surface, referred to generically as on, and the receptor film forms a high-impedance seal over at least the porous portion of the substrate. The porous portion sealed by the receptor film forms a highly sensitive sensor integral with the circuit of which the semiconductor substrate is a part. By sensor is intended a device which will detect the interaction of a chemical or biological moiety or a physical entity with the receptor film surface.

By receptor film is meant a film which is itself an active receptor or a film which incorporates a compound which is the receptor. The receptor is any compound, moiety, ligand, or material, referred to generically as compound(s), which will interact with a target to produce a current. The target can be of chemical, biological, or physical origin. The film can be any of a number of film forming compounds of both chemical and biological origin and combinations of these. In the usual case, the receptor compounds are incorporated into a film. These compounds are described in the prior art as detectors using electrodes, color changes or similar means to detect a target. As described herein, these prior art compounds are adapted to the invention.

The semiconductor substrate is any of the materials known to be useful in forming electronic devices which can be made porous and hydrophilic. The material must be capable of accepting the formation of a porous portion on its structure. These materials include the well known substrates such as silicon, germanium, aluminum containing materials, and ceramics Beale et al. in two articles "An Experimental and Theoretical Study of the formation of Microstructure of Porous Silicon", *Journal of Crystal Growth*, 73, 622 (1985) and "The Formation of Porous Silicon By Chemical Stain Etches", *Journal of Crystal Growth*, 75, 408 (1986), teaches it is possible to form pores in some compound semiconductors, and Beale suggests it should be possible to form pores in any semiconductor materials using an appropriate etchant and current density. Silicon is the preferred semiconductor substrate because it is easily and cheaply obtained, easy to make porous, and easy to make hydrophilic. In addition silicon and its oxide form stable devices It is preferred that the receptor containing film be a lipid, most preferably a lipid which can be polymerized. In the preferred form of the invention, a protein-lipid film is deposited onto an array of bipolar junction transistors (BJT's) which have had their base junctions converted to a porous, hydrophilic silica surface. This arrangement provides both the amplification of BJT circuits, the smaller geometry of microlithographically defined transistors, and the high impedance seal of silica with the lipid bilayers. The protein-lipids adhere very well to the surrounding silica surface affording a high impedance seal necessary for low noise operation of the device.

In general, the present invention is believed to operate on the theory that each receptor binding site and any associated ion channel spans the thickness of the film. When a chemical species of interest adsorbs on the receptor binding site, an ionic current flows through the receptor molecule or channel which spans the film thickness and directly enters the base of the substrate which is in the form of an electronic device, such as a transistor. This current flow is detected by the circuits which include that electronic device. In this invention a porous silicon surface is formed directly on the base of a bipolar junction transistor (BJT). Because the receptor is deposited on the transistor, the ionic current is directly injected into the transistor base. The intimate contact of the receptor molecules and the lipid bilayer with the transducing silicon electrode decreases leakage or background noise. Silicon fabrication technology makes it possible to fabricate noise-reducing circuitry directly with the transducing electrode. For this device, the signal current may be amplified without amplifying the system noise. When the receptor film is a lipid bilayer, the lipid bilayer serves as a seal against ion flow except through the ion channel.

In order for the lipids and receptors to behave properly, the silicon surface must be modified to accommodate them. The surface must be hydrophilic in order to deposit the lipid bilayer in the correct orientation; the surface must be porous to act as a conduit for the ion current flow; and the pores on the surface must be sufficiently small to lend structural support to the thin lipid bilayer.

The porous silicon can be made hydrophilic by converting the outer silicon layer to silica. The porous silicon surface can be converted to a hydrophilic silica surface simply by heating in an oxygen atmosphere. In addition to its other properties, the hydrophilic, porous portion or layer serves as a reservoir for the ionic solution.

The lipid bilayer is the thickness of two molecules, usually between 5 and 10 nm. This thickness is also applicable to other receptor films of this invention as a typical thickness which will permit the current flow with out undue loss by resistance. Preferably, the lipid layer should be approximately 7.5 nm thick.

The receptor employed in a lipid bilayer is a protein. A typical size of the protein is on the order of 5 nm, so that most of the pores in the porous portion can easily accommodate more than one protein. Microfabrication techniques can reduce the size of the semiconductor substrate in the form of a base down to 1000 to 2000 nm, so that several hundred pores may be included in any base. The pores in the silicon can be made from 1 to 1000 nm in diameter. The pores form a wormhole network into the bulk of the silicon substrate. However, the pore size is still small enough that the protein-lipid bilayer should not be susceptible to defects and tears. Preferably, the pore size should be less than 100 nm.

When silicon-based technology is used to make the electrode, temperature compensation circuits can be prepared as well as simple signal processing circuitry directly on the device. This provides higher performance and sensitivity over other conventional techniques. This invention offers four major advantages: (1) a hydrophilic, porous surface etched directly into silicon; (2) small pores size for structural support of the bilayer; (3) direct injection of the ion current into the amplifier; (4) reduced noise from both the intimate contact of the receptors with the transistor and the potential for the fabrication of signal processing circuitry directly with the electrode.

Now having generally described this invention, the following examples illustrate specific application of the invention.

EXAMPLE

The sensor is fabricated with a bipolar junction transistor. These are the building blocks for higher order signal processing circuitry. For example, a differential amplifier may be developed using this technology.

The basic technology for fabricating the substrate with a porous portion is described in such references such as Millman, *Microelectronics Digital and Analog Circuits and Systems*, McGraw-Hill Book Company, New York (1979) or Streetman, *Solid State Electronic Devices*, Prentice Hall Inc., Englewood Cliffs, N.J. (1972).

In an example illustrating the invention, a planar BJT (10) is fabricated in the npn configuration, as shown in FIG. 1 wherein a p-substrate (1) has an n-collector (2) formed in it. A p-base (3) is on the collector (2) and an n-emitter (4) is formed on the base (3). The emitter (4) contains a contact (5). A contact (6) is provided in the base.

In the alternative a pnp transistor may also be used. Any of the various technologies as described by Millman or Streetman may be used to fabricate the substrate and the circuitry to be developed from it.

Following the fabrication of the substrate, the surface is passivated with an insulating layer. This layer can be formed by several techniques including thermally growing a silicon dioxide layer directly on the surface or by depositing a silicon oxide, nitride, or any of the thin layer materials used to coat or passivate the silicon surface. It is preferred to use a thermally grown oxide in this description as illustrated in FIG. 2A.

Following deposition of the passivating layer, a hydrofluoric (HF) acid resistant layer is deposited on top of the passivating or insulating layer. This resistant layer can be a poly-silicon layer as illustrated in FIG. 2A, but any other film which is resistant to etching by HF acid will also work. The poly-silicon layer may be doped and grounded to act as a further shield for noise.

To form the desired patterns of receptor films, a photoresist is used to define an area over the base so the silicon base can be exposed by etching the poly-silicon and the oxide. The etching can be done by any known means such as chemical or ion bombardment. The resultant structure is illustrated in FIG. 2B.

Figure 3:
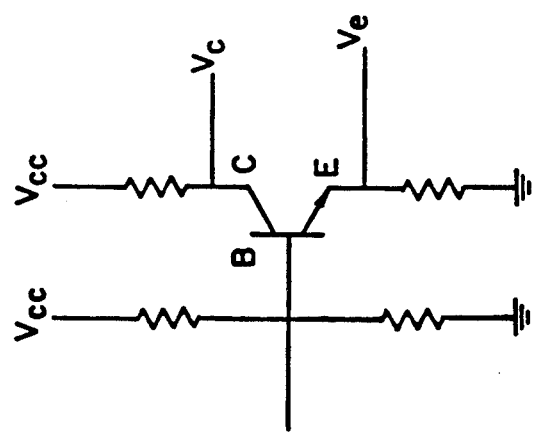
FIG. 3 is a wiring diagram illustrating one application of the sensor of this invention.

After the surface is etched to a desired pattern, a porous silicon surface is formed on the exposed base region by any means such as is taught by Beale et al., "Microstructure and Formation Mechanism of Porous Silicon," *Applied Physics Letters*, 46, pp. 86–8B (1985). The porous portion can be formed by a variety of means such as chemical etching, electrochemical etching, or ion bombardment. For the present invention electrochemical etching is preferred. To etch, an HF, ethanol, and water etching bath in the ratio of 2:1:1 is prepared; the ratio of the three may vary depending on the desired control on the quality of the smoothness of the silicon surface. A cathode electrode connected to a D.C. power supply (a battery) is placed in the etching bath; a platinum wire is used as the electrode. The base region of the transistor is connected with the anode either through one of the p-n junctions (the base-emitter or base-collector) for low-level current injection (or increased current with illumination); alternatively, it can be connected through a separate anodization pad which is provided for contact to the base as illustrated in FIG. 3 (i.e. through a biasing resistor).

Following the formation of the porous area, the device is placed into the etching bath. A current is passed from the anode (the silicon) to the cathode (the platinum) through the etching bath. Recommended current levels are on the order of 1 to 10 mA/cm$^2$ for a period of 1 to 10 minutes depending on the size of the pores and the depth of the porous silicon into the substrate desired. The sample is thoroughly rinsed with pure water after the etching process.

The porous silicon surface is now hydrophobic. As explained above, the surface must be hydrophilic. To make the surface hydrophilic, either a film, such as a metal or insulator which can be made hydrophilic, is deposited on the surface or a thin oxide layer is grown on the surface by chemical, thermal, or anodic techniques. The oxide thickness is preferrably less than the pore radius so the pores are kept open. The outer surface of the poly-silicon is made hydrophilic as well, preferably, during the same step that converts the porous silicon.

Care must be taken so as not to contaminate the surface. The simplest approach is to grow a very thin oxide by dipping the sample into concentrated nitric acid ($HNO_3$) or to heat the substrate to an elevated temperature in an oxygen atmosphere. After oxidation, the samples are aged in a solution such as water or phosphate buffered saline. The samples are now ready for deposition of the lipid bilayers and receptor proteins.

Bilayers are deposited by traditional Langmuir-Blodgett (LB) dipping techniques described by Gaines, Jr., *Insoluble Monolayers at Liquid-Gas Interfaces,* Interscience Publishers, New York (1966) or by a vesicle adsorption technique described by McConnell et al, "Supported Planar Membranes in Studies of Cell-Cell Recognition in the Immune System", Biochim. et Biophys. Acta, 864, pp. 95-106 (1986). For LB dipping, the receptors can be deposited directly with the monolayers from the air-water interface, or they can be incorporated afterwards by a detergent dialysis technique. For the vesicle adsorption technique, the receptors are incorporated directly with the adsorption of the vesicles onto the surface as illustrated in FIG. 4.

In use, the device is placed into a reference bath having a controlled pH, temperature, and/or ionic strength. As illustrated in FIGS. 3, 5, and 6 the sensor (10) of this invention is shown in the form of an amplifier. A reference electrode (11) is in the test solution (20) with the sensor (10). Both the sensor and reference electrode are connected to the processing and display apparatus (12) in such a manner that any signal generated on the receptor is displayed on the display apparatus. The particular device illustrated in FIG. 5 is operated in the so-called common emitter configuration. A reference electrode (11) (silver-silver chloride) is used to bias the base-emitter junction (see FIG. 5). The device is operated by measuring the voltage at the collector, $V_c$, or at the emitter, $V_e$ as illustrated in FIG. 3. Whenever a current is induced to flow from the reference electrode to the transistor through the base circuit, a change in $V_c$ or $V_e$ can be measured. This can be done in two modes:

The D.C. Mode: When an ion channel opens in a receptor, it is measured as a square-wave current pulse using a patch clamp electrode. Using the porous electrode described here, the current injected into the base will be amplified by the transistor and appear as a pulse at the collector or emitter node.

The A.C. Mode: A sinusoidal wave signal is applied to the reference electrode so that an A.C. signal is caused to flow in the transistor circuit. Again, when an ion channel opens in the base region, the current pulse may measured as a change in the voltage $V_c$ or $V_e$. In this, however, the impedance of the protein-lipid film can as a check on the electrical quality of film over the lifetime of the device.

The use of the porous silicon substrate permits the fabrication of circuits directly into the to reduce the noise in the measurement. Advantage can be the BJT as a building block for more signal processing circuitry.

FIGS. 5 and 6 illustrate an alternative application for this invention as a differential amplifier. With this circuitry, circuit noise can be reduced by subtracting the difference in the signals that occur at the respective base regions 1 and 2 as illustrated in FIG. 6. By blanking off base 2, the receptor signal at base 1 can be amplified without amplifying the noise at the inputs. More complex circuitry may be added a temperature compensation or for arrays of receptors or chemically sensitive layers. Silicon is sensitive to light and alternatively, circuitry may be used for detecting photo-act species which are bound to the surface. The light would directly couple into the transistor as they are bound to the base.

Beside forming the porous portion in the substrate itself, the semiconductor material can be deposited onto a another form of substrate and it may be made porous. For example, one may deposit an insulator with added impurities (for example), a glass heavily doped with impurities) and form a porous layer by removing the aggregated impurities, analogous to the technique use to form porous glass beads. Or, one may deposit a thin aluminum layer, and form porous alumina by an electrochemical etching technique described by Miller and M. Majda, "Microporous Aluminum Oxide Films at Electrodes", Journal of Electroanalytical Chemistry, 27, pp. 49-72 (1986).

Obviously, many modifications and variations of the present invention are possible in light of the above teachings. It is therefore to be understood that within the scope of the appended claims, the invention may be practiced otherwise than as specifically described.

What is claimed is:

1. An amperometric sensor comprising:
   a semiconductor substrate having a nonporous portion and a hydrophilic porous portion on said nonporous portion, and
   a high impedance receptor film in intimate contact with and sealing at least the porous portion, said receptor film permitting a significant ionic current to enter said porous portion only in response to an interaction of said receptor film with a predetermined chemical.

2. A sensor according to claim 1 wherein the semiconductor substrate is silicon.

3. A sensor according to claim 1 wherein the receptor film is a Langmuir-Blodgett type film.

4. A sensor according to claim 2 wherein the receptor film is a Langmuir-Blodgett type film.

5. A sensor according to claim 3 wherein the film is formed from a lipid.

6. A sensor according to claim 4 wherein the film is formed from a lipid.

7. A sensor according to claim 6 wherein the film is a bilayer.

8. A sensor according to claim 2 wherein the semiconductor substrate is in the form of a bipolar junction transistor.

9. A sensor according to claim 8 wherein the receptor film is a Langmuir-Blodgett type film.

10. A sensor according to claim 9 wherein the film is formed from a lipid.

11. A sensor according to claim 10 wherein the film is a bilayer.

12. The sensor of claim 1, wherein said receptor film comprises a lipid bilayer including a receptor protein.

13. The sensor of claim 1, wherein the pores of said hydrophilic porous portion form a wormhole network.

14. The sensor of claim 13, wherein the pores of said hydrophilic porous portion have diameters of from 1 to 1000 nm.

15. The sensor of claim 14, wherein the pores of said hydrophilic portion have diameters of less than 100 μm.

16. An amperometric, receptor-based sensor comprising:
   a semiconductor substrate having a nonporous portion and a hydrophilic porous portion, and a high impedance receptor film covering at least the porous portion, said receptor film permitting a significant ionic current to enter said porous portion only in response to an interaction of said receptor film with a predetermined chemical.

17. The sensor of claim 16, wherein said receptor film comprises a lipid bilayer including a receptor protein.

18. The sensor of claim 16, wherein the pores of said hydrophilic porous portion have diameters of from 1 to 1000 nm.

19. The sensor of claim 1, wherein the pores of said hydrophilic porous portion form a wormhole network.

20. A method of making an amperometric receptor-based sensor comprising the steps of:
forming a nonporous semiconductor substrate;
forming a hydrophilic porous portion on a surface of said nonporous semiconductor substrate; and
sealing at least the hydrophilic porous portion with a layer of high-impedance receptor film which permits a significant ionic current to enter the porous portion only in response to the interaction of said receptor film with a chemical of interest.

21. The method of claim 20, wherein said receptor film comprises a lipid bilayer including a receptor protein.

22. The method of claim 20, wherein the pores of said hydrophilic porous portion form a wormhole network.

23. The method of claim 22, wherein the pores of said hydrophilic porous portion have diameters of from 1 to 1000 nm.

24. The method of claim 23, wherein the pores of said hydrophilic portion have diameters of less than 100 μm.

25. The method of claim 20, wherein said hydrophilic porous portion is in intimate contact with said semiconductor substrate and said receptor film is in intimate contact with said hydrophilic porous portion.

26. The sensor of claim 2, wherein the porous hydrophilic portion is made by a method comprising the step of etching an outer, nonporous silicon layer of said substrate to produce a porous silicon layer and then growing a outer layer of oxide on an outer layer of said porous silicon layer.

27. The method of claim 20, wherein said nonporous semiconductor substrate is silicon and said hydrophilic porous portion is made by a method comprising the step of etching an outer, nonporous silicon layer of said substrate to produce a porous silicon layer and then growing a outer layer of oxide on an outer layer of said porous silicon layer.

* * * * *